(12) United States Patent
Tanaka et al.

(10) Patent No.: US 9,574,168 B2
(45) Date of Patent: *Feb. 21, 2017

(54) CELL COLLECTION METHOD

(71) Applicant: Toyo Seikan Group Holdings, Ltd., Tokyo (JP)

(72) Inventors: Satoshi Tanaka, Kanagawa (JP); Ryo Suenaga, Kanagawa (JP); Masahiro Kuninori, Kanagawa (JP); Kyohei Ota, Kanagawa (JP)

(73) Assignee: TOYO SEIKAN GROUP HOLDINGS, LTD., Tokyo (JP)

(*) Notice: Subject to any disclaimer, the term of this patent is extended or adjusted under 35 U.S.C. 154(b) by 136 days.

This patent is subject to a terminal disclaimer.

(21) Appl. No.: 14/341,543

(22) Filed: Jul. 25, 2014

(65) Prior Publication Data

US 2014/0335600 A1    Nov. 13, 2014

Related U.S. Application Data

(63) Continuation of application No. PCT/JP2013/000462, filed on Jan. 29, 2013.

(30) Foreign Application Priority Data

Feb. 1, 2012 (JP) ................... 2012-019951
Feb. 1, 2012 (JP) ................... 2012-020326

(51) Int. Cl.
*C12N 1/02* (2006.01)
*C12M 1/00* (2006.01)
*C12M 1/26* (2006.01)

(52) U.S. Cl.
CPC ............. *C12N 1/02* (2013.01); *C12M 23/14* (2013.01); *C12M 33/18* (2013.01)

(58) Field of Classification Search
None
See application file for complete search history.

(56) References Cited

U.S. PATENT DOCUMENTS

| | | | | |
|---|---|---|---|---|
| 5,523,228 A | * | 6/1996 | Ingram | C12M 23/14 435/297.1 |
| 6,673,598 B1 | * | 1/2004 | Akers | C12M 23/14 435/297.2 |
| 2010/0075406 A1 | * | 3/2010 | Tanaka | C12M 23/14 435/287.1 |
| 2013/0109086 A1 | | 5/2013 | Kobayashi et al. | |

FOREIGN PATENT DOCUMENTS

| | | |
|---|---|---|
| EP | 2141226 A1 | 1/2010 |
| JP | 2000125848 A | 5/2000 |
| JP | 2001275659 A | 10/2001 |
| JP | 2006094718 A | 4/2006 |
| JP | 2007175028 A | 7/2007 |
| JP | 2010075115 A | 4/2010 |
| WO | 2007052716 A1 | 5/2007 |
| WO | 2008136371 A1 | 11/2008 |
| WO | 2009104296 A1 | 8/2009 |
| WO | 2012002497 A1 | 1/2012 |

OTHER PUBLICATIONS

International Search Report issued in PCT/JP2013/000462 mailed Feb. 26, 2013 (4 pages).
International Preliminary Report on Patentability and Written Opinion issued in PCT/JP2013/000462 mailed Aug. 14, 2014 (10 pages).
Extended European Search Report issued in corresponding European Application No. 13743310.8 dated Aug. 14, 2015 (12 pages).

* cited by examiner

*Primary Examiner* — Renee Claytor
*Assistant Examiner* — Sharon M Papciak
(74) *Attorney, Agent, or Firm* — Osha Liang LLP (57) ABSTRACT

A method for collecting cells that have been cultured by using a cell culture kit in which, at least, a culture container for cultivating cells, a cell collection container for collecting cells after cultivation and a waste liquid container for collecting a culture medium after cultivation are linked to one another through a conduit is provided. The method includes transferring a culture supernatant that has been cultured from the culture container to the waste liquid container, transferring a concentrated suspension of cells from the culture container to the cell collection container, returning part of the culture supernatant discharged in the waste liquid container to the culture container and allowing cells remaining in the culture container to be suspended in a suspension of cells, and transferring again a suspension of cells in which remaining cells are suspended from the culture container to the cell collection container.

11 Claims, 4 Drawing Sheets

| Experiment conditions | Culture container 22×66cm |  |  |  |  |
| --- | --- | --- | --- | --- | --- |
|  | Amount of culture liquid 2000mL |  |  |  |  |
|  | Number of cells 8.00E+09 |  |  |  |  |
| (Comparative Example 1) Collection by washing is not conducted |  | Capacity (mL) | Density (*10^4) | Number of cells | Percentage (%) |
|  | Waste liquid container | 1600 | 12.5 | 2.00E+08 | 2.5 |
|  | Collection container | 350 | 1950 | 6.83E+09 | 85.31 |
|  | Culture container | 50 | 1950 | 9.75E+08 | 12.19 |
|  | Total | 2000 |  |  | 100 |
| (Example 1) Collection by washing is conducted once |  | Capacity (mL) | Density (*10^4) | Number of cells | Percentage (%) |
|  | Waste liquid container | 1550 | 12.5 | 1.94E+08 | 2.42 |
|  | Collection container | 400 | 1950 | 7.32E+09 | 91.45 |
|  | Culture container | 50 | 981.25 | 4.91E+08 | 6.13 |
|  | Total | 2000 |  |  | 100 |
| (Example 2) Collection by washing is conducted twice |  | Capacity (mL) | Density (*10^4) | Number of cells | Percentage (%) |
|  | Waste liquid container | 1500 | 12.5 | 1.88E+08 | 2.34 |
|  | Collection container | 450 | 1950 | 7.56E+09 | 94.55 |
|  | Culture container | 50 | 496.88 | 2.48E+08 | 3.11 |
|  | Total | 2000 |  |  | 100 |
| (Example 3) Collection by reduction is conducted |  | Capacity (mL) | Density (*10^4) | Number of cells | Percentage (%) |
|  | Waste liquid container | 1600 | 12.5 | 2.00E+08 | 2.5 |
|  | Collection container | 390 | 1950 | 7.61E+09 | 95.06 |
|  | Culture container | 10 | 1950 | 1.95E+08 | 2.44 |
|  | Total | 2000 |  |  | 100 |
| (Example 4) Collection by reduction and collection by washing are conducted once |  | Capacity (mL) | Density (*10^4) | Number of cells | Percentage (%) |
|  | Waste liquid container | 1590 | 12.5 | 1.99E+08 | 2.48 |
|  | Collection container | 400 | 1950 | 7.70E+09 | 96.29 |
|  | Culture container | 10 | 981.25 | 9.81E+07 | 1.23 |
|  | Total | 2000 |  |  | 100 |

CELL COLLECTION METHOD

CROSS-REFERENCE TO RELATED APPLICATIONS

This application claims the benefit of International Patent Application No. PCT/JP2013/000462, filed on Jan. 29, 2013, which is incorporated by reference in its entirety.

TECHNICAL FIELD

The present invention relates to a method for collecting cells that have been cultivated by using a culture container. In particular, the present invention relates to a method for collecting cells that enables cell collection efficiency to be improved.

BACKGROUND ART

In recent years, in the fields of production of medicines, gene therapy, regenerative medicine, immunotherapy or the like, there has been a demand for cultivating a large amount of cells, tissues, microorganisms or the like efficiently in an artificial environment.

In such cultivation of a large amount of cells, in general, cells are cultivated by using a culture container. In the cell culture by using a culture container, it is required to collect cells from the culture container after cultivation.

In the case where cultured cells (in particular, floating cells) are collected, conventionally, a method was conducted in which the total amount of a suspension of cells is collected from a culture container, and cells are then separated by centrifugation. However, this method suffers from a problem that, when a large amount of a suspension of cells is present due to the cultivation of a large amount of cells, centrifugation is required to be conducted several times in a divided manner, resulting in waste of time and effort.

On the other hand, as a technology relating to the method for collecting cells, a cell collection method used in the cell culture method disclosed in Patent Document 1 can be given, for example. In this collection method, after discharging a used culture medium supernatant from a culture container, a suspension containing cultured cells is collected, whereby a concentrated suspension of cells can be obtained.

RELATED ART DOCUMENT

Patent Document

Patent Document 1: WO2007/052716

SUMMARY OF THE INVENTION

Problems to be Solved by the Invention

However, this method has a problem that a relatively large amount of cells remains in the culture container that are not collected, resulting in insufficient collection efficiency.

Specifically, according to this collection method, although it is possible to collect a concentrated suspension of cells, even if a suspension of cells is collected, there are some cells that remain in a culture container in the state where they adhere to the wall of the container. Further, this method also has a problem that, if the culture container is formed of a flexible material, when the amount of a suspension of cells becomes small, the inside of the culture container tends to be blocked easily, and as a result, a relatively large amount of a suspension of cells remains in the culture container to cause cells to remain within the culture container.

In order to solve such a problem, it is conceivable to use a method in which, after collecting a suspension of cells, a new washing liquid (physiological saline or phosphate buffer) is put to a culture container, followed by stirring, whereby cells remaining in the culture container are suspended in the washing liquid to conduct collection again. However, in such a method in which cells remaining in the culture container are collected by using a washing liquid, a new washing liquid or washing liquid storage container for storing it has become required, resulting in an increase in cost.

The present invention has been made in view of the above-mentioned circumstances, and is aimed at providing a method for collecting cells that can prevent blocking of a culture container and can improve cell collection efficiency without using a new culture medium or washing liquid for washing purposes.

Means for Solving the Problem

In order to attain the above-mentioned objects, the method for collecting cells of the present invention is a method for collecting cells that have been cultured by using a cell culture kit in which, at least, a culture container for cultivating cells, a cell collection container for collecting cells after cultivation and a waste liquid container for collecting a culture medium after cultivation are linked to one another through a conduit, that comprises:

a supernatant discharge step for transferring a culture supernatant that has been cultured from the culture container to the waste liquid container;

a cell collection step for transferring a concentrated suspension of cells from the culture container to the cell collection container;

a supernatant returning step for returning part of the culture supernatant discharged in the waste liquid container to the culture container and allowing cells remaining in the culture container to be suspended in a suspension of cells; and a re-collection step for transferring again a suspension of cells in which remaining cells are suspended from the culture container to the cell culture container.

Further, the method for collecting cells of the present invention is a method for collecting cells that are cultivated by using a cell culture kit in which, at least, a culture container for cultivating cells, a cell collection container for collecting cells after cultivation and a waste liquid container for collecting a culture medium after cultivation are linked to one another through a conduit, that comprises:

a supernatant discharge step for transferring a culture supernatant that has been cultured from the culture container to the waste liquid container;

a reduction step for reducing the bottom surface area of the culture container, whereby a concentrated suspension of cells is gathered to the cell collection port side of the culture container; and a collection by reduction step for transferring the gathered suspension of cells from the culture container to the cell collection container.

Advantageous Effects of the Invention

According to the present invention, when collecting cells that are cultured by using a culture container, blocking of a culture container can be suppressed, and cell collection efficiency can be improved without using a new cultivation medium or a washing liquid for washing purposes.

MODE FOR CARRYING OUT THE INVENTION

Hereinbelow, an explanation will be made on preferred embodiments of the present invention with reference to the drawings. First, by referring to FIG. 1, an explanation will be made on a cell culture kit that can preferably be used in the method for collecting cells of this embodiment. This cell culture kit is provided with a culture container 10, a culture medium storage container 20, a cell injection container 30, a cell collection container 40, a sampling container 50 and a tube 60. The culture medium storage container 20 is also used as a waste liquid container.

Figure 1:
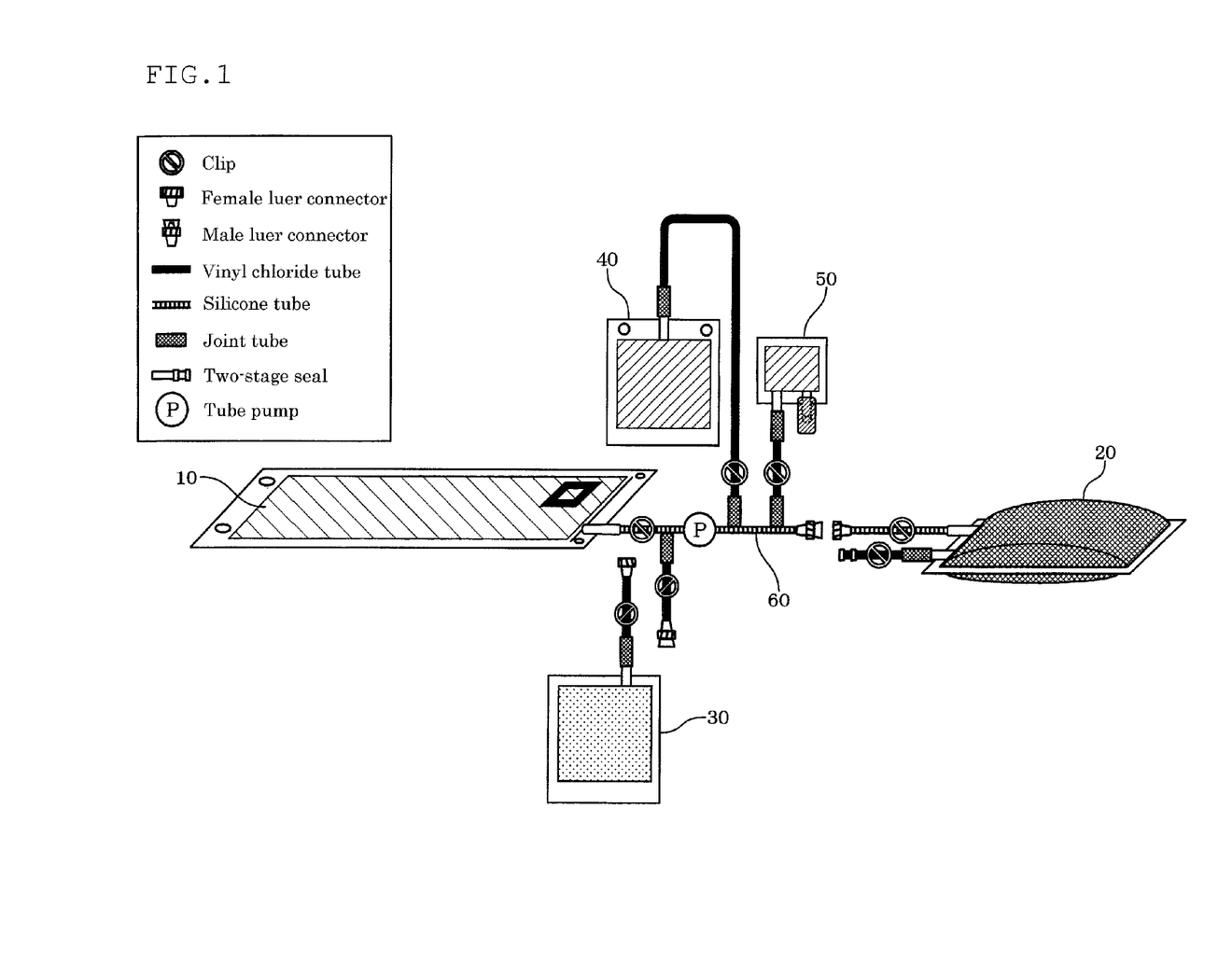
FIG. 1 is a view showing a cell culture kit used in the method for collecting cells of the embodiments of the present invention.

The method for collecting cells of this embodiment is a method which is used, after cell culture is conducted by using such a cell culture kit, for collecting cells from the culture container 10 to the cell collection container 40 in the cell culture kit.

The cell culture kit used in the method for collecting cells in this embodiment is not limited to such a configuration, and it is possible to add appropriate modifications to a kit; specifically, it is also possible to use a kit that does not have the sampling container 50; a kit provided with a waste liquid container separately from the culture medium storage container; and a kit provided with a plurality of the culture medium storage containers 20.

The culture container 10 is a container in which cells to be cultured and a culture medium are placed in order to cultivate a large amount of cells. The culture container 10 is made of a flexible material and is formed in a bag.

This culture container 10 is provided with a port for injecting or collecting a culture medium or cells. The number of ports is not particularly restricted, but a culture container having one to three ports can preferably be used. FIG. 1 shows a one-port cell culture kit. In this kit, transfer of a culture medium, a suspension of cells or the like to other containers can be conducted through this port while keeping a closed system.

As cells to be cultured, floating cells can preferably be used. Various common culture mediums can be used as a culture liquid.

The culture medium storage container 20 is a container for storing a culture liquid (culture medium) for cultivating cells in order to transfer it to the culture container 10. The culture medium storage container 20 can be used as a waste liquid container after completion of cultivation. That is, prior to collection of cells from the culture container 10 to the cell collection container 40, by transferring a supernatant of the culture liquid to culture medium storage container 20 as the waste liquid container, a concentrated suspension of cells can be sent from the culture container 10 to the cell collection container 40.

In the cell culture kit of this embodiment, two or more of the culture medium storage containers 20 can be provided. Due to such a configuration, not only twice the amount of the same culture liquid can be stored but also, by storing different culture liquids in different storage containers, a culture liquid can be supplied to the culture container 10 in various modes.

The cell injection container 30 is a container in which cells and a culture medium that are required at the time of starting cultivation are placed. By transferring the cells and the culture medium in this cell injection container 30 to the culture container 10, cultivation of cells starts. The cell injection container 30 is provided with at least one port, and the cells and the culture medium are transferred through this port.

The cell collection container 40 is a container for collecting a suspension of cells that contains part of the culture medium and cultured cells after completion of cultivation. The cell collection container 40 is provided with at least one port, and suspension of cells containing part of the culture medium and cultured cells is transferred from the culture container 10 to the cell collection container 40 through this port.

The sampling container 50 is a container for conducting sampling. Specifically, during or after cultivation of cells, part of a suspension of cells in the culture container 10 is transferred to the sampling container 50 for sampling. A suspension of cells as a sample to be transferred to this sampling container 50 contains cultured cells and a culture medium. The sampling container 50 is provided with at least one port to which a conduit (tube) that is linked to the culture container 10 is connected, and a suspension of cells is sent from the culture container 10 to the sampling container 50.

A tube 60 is a conduit that links containers in the cell culture kit.

Figure 2:
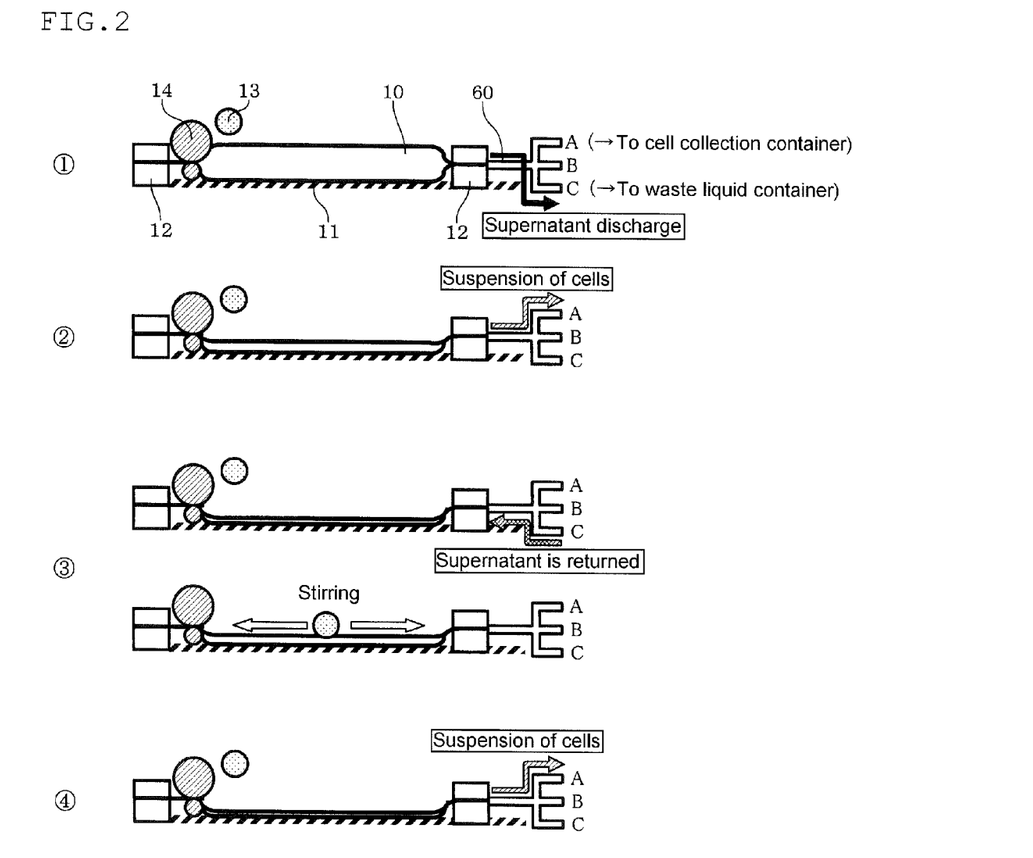
FIG. 2 is a view showing a procedure of collection by washing in the method for collecting cells according to the first embodiment of the present invention.

Subsequently, a configuration of a cell culture device by which the method for collecting cells of this embodiment is implemented will be explained with reference to FIG. 2. FIG. 2 diagrammatically shows a cell culture device. In this cell culture device, the culture container 10 in the above-mentioned cell culture kit is arranged, whereby cultivation of cells is conducted. As shown in FIG. 2, the cell culture device is provided with the culture container 10, a mounting table 11, a fixing element 12, a stirring element 13, a partition element 14 and the tube 60.

The mounting table 11 is a flat table in which the culture container 10 is mounted on the upper surface thereof and, further, on the upper surface of the culture container 10, a stirring element 13 or a partition element 14 is provided.

The fixing element 12 is an element for fixing the culture container 10 to the mounting table 11. In FIG. 2, the fixing element 12 is shown as a clamp. However, it can be configured as a stopping element (e.g. pin) that passes through holes provided in the four corners of the culture container 10 for fixing.

The stirring element 13 serves to stir a suspension of cells in the culture container 10 by applying an external force to the culture container 10. As a result, cells in the culture container 10 are dispersed in a suspension of cells, thereby to make it to be transferred easily to the cell collection container 40. Further, cells that are adhering to the inner wall of the culture container 10 are dispersed in a suspension of cells, whereby the cells are enabled to be transferred to the cell collection container 40 easily. Stirring of a suspension of cells in the culture container 10 by means of the stirring element 13 can be conducted at an appropriate timing, e.g. prior to the transfer of a suspension of cells.

As this stirring element 13, a roller can be used, for example. The upper surface of the culture container 10 is pressed by the stirring element 13 to a predetermined depth, and the stirring element 13 is allowed to move in parallel with the mounting table 11, whereby a suspension of cells can be stirred.

Although not shown, the stirring element 13 can be placed on the culture container 10 by means of a supporting table. By allowing this supporting table to move in the vertical direction and the horizontal direction by means of a driving apparatus, stirring by means of the stirring element 13 can be conducted.

The partition element 14 presses the culture container 10 from the end portion of the culture container 10 until the upper surface and the lower surface of the culture container 10 are brought into close contact with each other, and is allowed to move in the horizontal direction relative to the mounting table 11, thereby to increase or decrease the bottom surface area of the culture container 10.

Since the culture container 10 is formed of a flexible material, if the bottom surface area of the culture container 10 is decreased by the partition element 14, a suspension of cells is pushed upward in the culture container 10, whereby the thickness of the culture container 10 is slightly increased.

In the reduction step mentioned later, by reducing the bottom surface area of the culture container 10 and increasing the liquid thickness of a suspension of cells in the culture container 10, occurrence of blocking in the culture container 10 can be prevented. As a result, the amount of a suspension of cells to be collected from the culture container 10 to the cell collection container 40 is increased, and hence, collection efficiency of cells can be improved.

In the standstill step mentioned later, after allowing the container to stand in the state where the bottom surface area of the culture container 10 is reduced to increase the liquid thickness of a suspension of cells in the culture container 10, a culture supernatant of a suspension of cells in the culture container 10 can be transferred to a waste liquid container.

By conducting transfer of a culture supernatant to the waste liquid container in the above-mentioned way, as compared with a case where a culture supernatant is transferred to the waste liquid container without reducing the bottom surface area of the culture container 10, the concentration of cells in a suspension of cells remaining in the culture container 10 after discharge of a supernatant can be increased.

The reason therefor is as follows. The amount of a culture supernatant relative to the bottom surface in the culture container 10 can be increased, and as result, the amount of a culture supernatant to be discharged can be increased. As a result, the concentration of cells in a suspension of cells to be collected in the cell collection container 40 is increased, whereby the amount of a suspension of cells to be collected can be small.

This partition element 14 can be configured as a roller or the like as in the case of the stirring element 13. FIG. 2 shows the partition element 14 that vertically holds the culture container 10 by two rollers. The partition element 14 is not restricted to that shown in FIG. 2, and any configuration is possible as long as it can reduce the bottom surface area of the culture container 10. The partition element 14 can be driven in the same way as in the case of the stirring element 13.

In FIG. 2, the tube 60 links the culture container 10, the cell collection container, the waste liquid container or the like. In an example shown in FIG. 2, the tube 60 is divided into A, B and C, and A is linked to the cell collection container and C is linked to the waste liquid container. B can be used as one that is linked to the sampling container, for example.

First Embodiment

Next, the first embodiment of the method for collecting cells of the present invention will be explained with reference to FIG. 2. In the present specification, the method for collecting cells including the following supernatant returning step and re-collection step may often be referred to as the "collection by washing".

(1) Supernatant Discharge Step

First, after causing cells to settle in the lower part of the container by allowing the culture container 10 to stand, a supernatant of a suspension of cells is transferred from the culture container 10 to the waste liquid container.

As a result, a suspension of cells in the culture container 10 can be concentrated, whereby the concentration of cells can be increased. The discharge of a culture supernatant can be conducted by actuating a tube pump in the tube 60. The transfer of a suspension of cells or returning of a culture supernatant explained below can be conducted by actuating a tube pump in the tube 60.

(2) Cell Collection Step

Subsequently, from the culture container 10, a suspension of cells is transferred to the cell collection container. In the state where this transfer is completed, in the culture container 10, part of a suspension of cells containing cultured cells remains.

(3) Supernatant Returning Step

Subsequently, part of a culture supernatant is returned from the waste liquid container to the culture container 10, and the culture container 10 is stirred by means of the stirring element 13. As a result, cells remaining in the culture container 10, such as cells adhering to the wall of the culture container 10, can be suspended in a suspension of cells. Stirring may be conducted according to need.

(4) Re-Collection Step

Subsequently, a suspension of cells in which remaining cells are suspended is transferred again from the culture container 10 to the cell collection container. As a result, according to the cell collection method of this embodiment, cells remaining in the culture container 10 during the cell collection step can be collected without using a new culture medium or a washing liquid, whereby collection efficiency of cells can be improved.

In the above-mentioned method for collecting cells, it is preferred that the supernatant returning step and the re-collection step be repeated twice or more. By repeating the supernatant returning step and the re-collection step twice or more, cells remaining in the culture container 10 can be further collected each time, whereby collection efficiency can be further improved.

Further, in the above-mentioned cell collection method, it is preferred that the supernatant returning step and the re-collection step be conducted simultaneously. By conducting the supernatant returning step and the re-collection step simultaneously, cells are re-collected while flowing a culture supernatant, whereby cells remaining in the culture container 10 can be transferred easily to the cell collection container 40. At this time, as the culture container 10, one having two or more ports can preferably be used. Through the tube 60, one port is linked to the cell collection container 40 and another port is linked to the waste liquid container.

Second Embodiment

Figure 3:
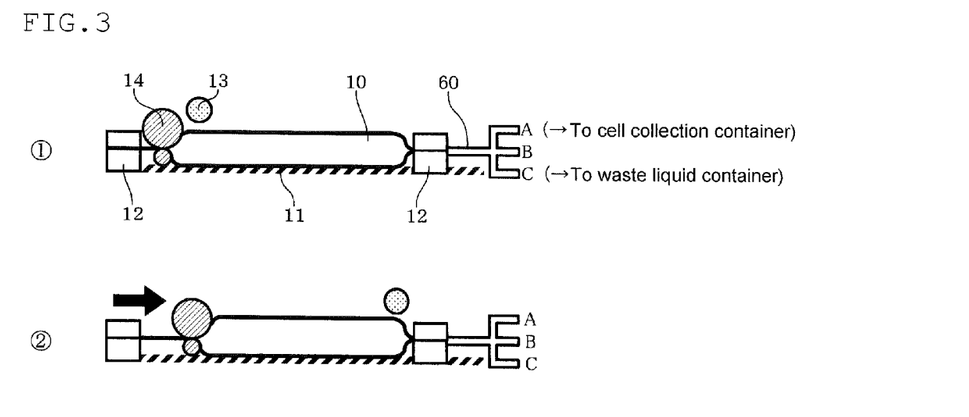
FIG. 3 is a view showing a procedure of allowing a culture container to stand in the method for collecting cells according to the second embodiment of the present invention.

Subsequently, the second embodiment of the method for collecting cells of the present invention will be explained with reference to FIG. 3.

As mentioned below, the method for collecting cells of this embodiment differs from the first embodiment in that the standstill step is conducted prior to the supernatant discharge step. Other points are the same as those in the first embodiment.

(1) Standstill Step

Before conducting the supernatant discharge step in the cell collection method of the first embodiment, the bottom surface area of the culture container 10 is reduced by means of the partition element 14. Specifically, by means of the partition element 14, from the end portion of the culture container 10, while bringing the upper surface and the lower surface of the culture container 10 into close contact with each other, the partition element 14 is allowed to move on the culture container 10, whereby the bottom surface area of the culture container 10 can be reduced. Then, the culture container 10 is allowed to stand to cause cells to settle in the lower part of the container.

Thereafter, the supernatant discharge step, the cell collection step, the supernatant returning step and the re-collection step as explained in the first embodiment are conducted. It is also preferred that the supernatant returning step and the re-collection step be conducted repeatedly.

By conducting collection by washing after reducing the bottom surface area of the culture container 10 as mentioned above, the amount of a supernatant relative to the bottom surface area can be increased, whereby the amount of a discharged culture supernatant can be increased. Therefore, the concentration of cells in a suspension of cells to be collected in the cell collection step can be increased, whereby collection efficiency of cells can be improved.

Third Embodiment

Figure 4:
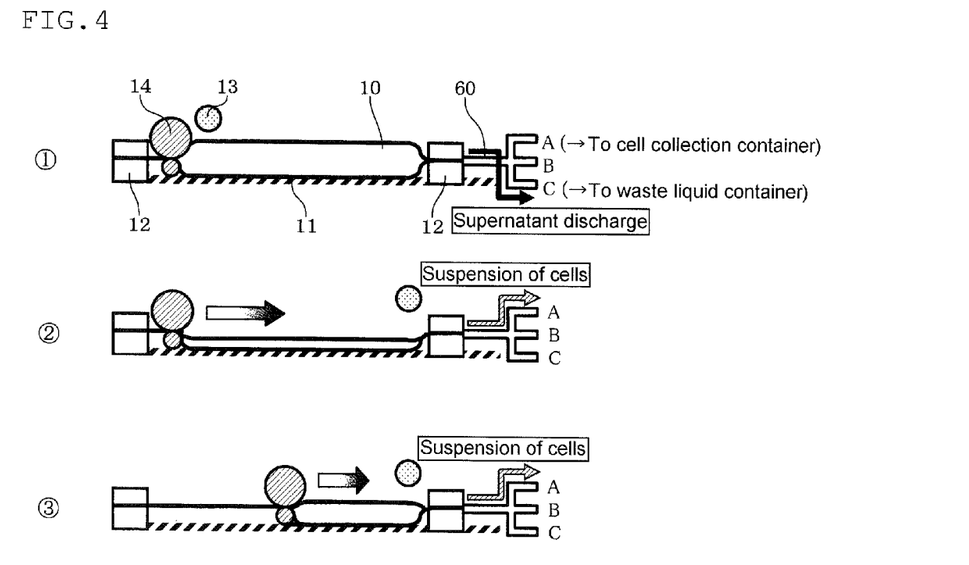
FIG. 4 is a view showing a procedure of collection by reduction according to the third embodiment of the present invention.

Subsequently, the third embodiment of the method for collecting cells will be explained with reference to FIG. 4. In the present specification, the method for collecting cells including the following reduction step and collection by reduction step may often be referred to as the "collection by reduction".

(1) Supernatant Discharge Step

First, as in the case of the first embodiment, after causing cells to settle in the lower part by allowing the culture container 10 to stand, a supernatant of a suspension of cells is transferred from the culture container 10 to the waste liquid container.

(2) Step of Reducing the Bottom Surface Area (Hereinafter Abbreviated as the "Reduction Step")

Subsequently, the bottom surface area of the culture container 10 is reduced by means of the partition element 14. Specifically, by means of the partition element 14, from the end portion of the culture container 10, while bringing the upper surface and the lower surface of the culture container 10 into close contact with each other, the partition element 14 is allowed to move on the culture container 10, whereby the bottom surface area of the culture container 10 can be reduced. As a result, a suspension of cells can be gathered in a position near a cell collection port or on the side of a cell collection port in the culture container 10.

(3) Step of Collection by Reducing the Bottom Surface Area (Hereinafter Abbreviated as the "Collection by Reduction")

Further, in the state where the bottom surface area of the culture container 10 is reduced, a suspension of cells is transferred from the culture container 10 to the cell collection container 40. As mentioned above, by conducting transfer of a suspension of cells in the state where the bottom surface area of the culture container 10 is reduced, blocking of the culture container 10 due to a decrease in the liquid amount of a suspension of cells (liquid thickness) can be suppressed. As a result, the amount of a suspension of cells remaining in the culture container 10 can be reduced, whereby cell collection efficiency can be improved.

Further, it is preferred that the reduction step and the collection by reduction step be conducted simultaneously. That is, it is preferred that, by means of the partition element 14, while reducing the bottom surface area of the culture container 10, a suspension of cells be transferred from the culture container 10 to the culture collection container 40. By conducting simultaneously the reduction step and the collection by reduction step, blocking of the culture container 10 can be suppressed.

Further, it is also preferred that, after the supernatant discharge step, the cell collection step in which a concentrated suspension of cells is transferred from the culture container 10 to the cell collection container 40 be conducted, and subsequently, the reduction step and the collection by reduction step be conducted. By this, it is possible to collect cells by suppressing blocking of the culture container 10.

As mentioned above, according to the cell collection method of this embodiment, the amount of a suspension of cells remaining in the culture container 10 can be reduced by suppressing blocking of the culture container, whereby collection efficiency of cells can be improved without using a new culture medium or a washing liquid for washing purposes.

Fourth Embodiment

Next, an explanation will be made on the fourth embodiment of the method for collecting cells of the present invention. The method for collecting cells of this embodiment differs from that of the third embodiment in that the first embodiment is added to the third embodiment, whereby collection by washing is conducted after collection by reduction. Other points are the same as those of the third embodiment.

That is, in the cell collection method of this embodiment, first, after conducting the supernatant discharge step, the reduction step and the collection by reduction step, the supernatant returning step and the re-collection step of the first embodiment are conducted.

As a result, not only blocking of the culture container is suppressed and the amount of a suspension of cells remaining in the culture container 10 is reduced to improve collection efficiency of cells but also, by washing the culture container 10 to allow cells adhering to the wall to be suspended in a suspension of cells, cell collection efficiency can be improved.

According to the method for collecting cells of this embodiment, cell collection efficiency can be further improved without using a new culture medium or a washing liquid for washing purposes.

In addition, by combining the method for collecting cells of this embodiment with the second embodiment to attain a configuration in which the collection by reduction step is conducted after conducting the standstill step, and then the collection by washing is conducted, cell collection efficiency can be further improved.

EXAMPLES

Figure 5:
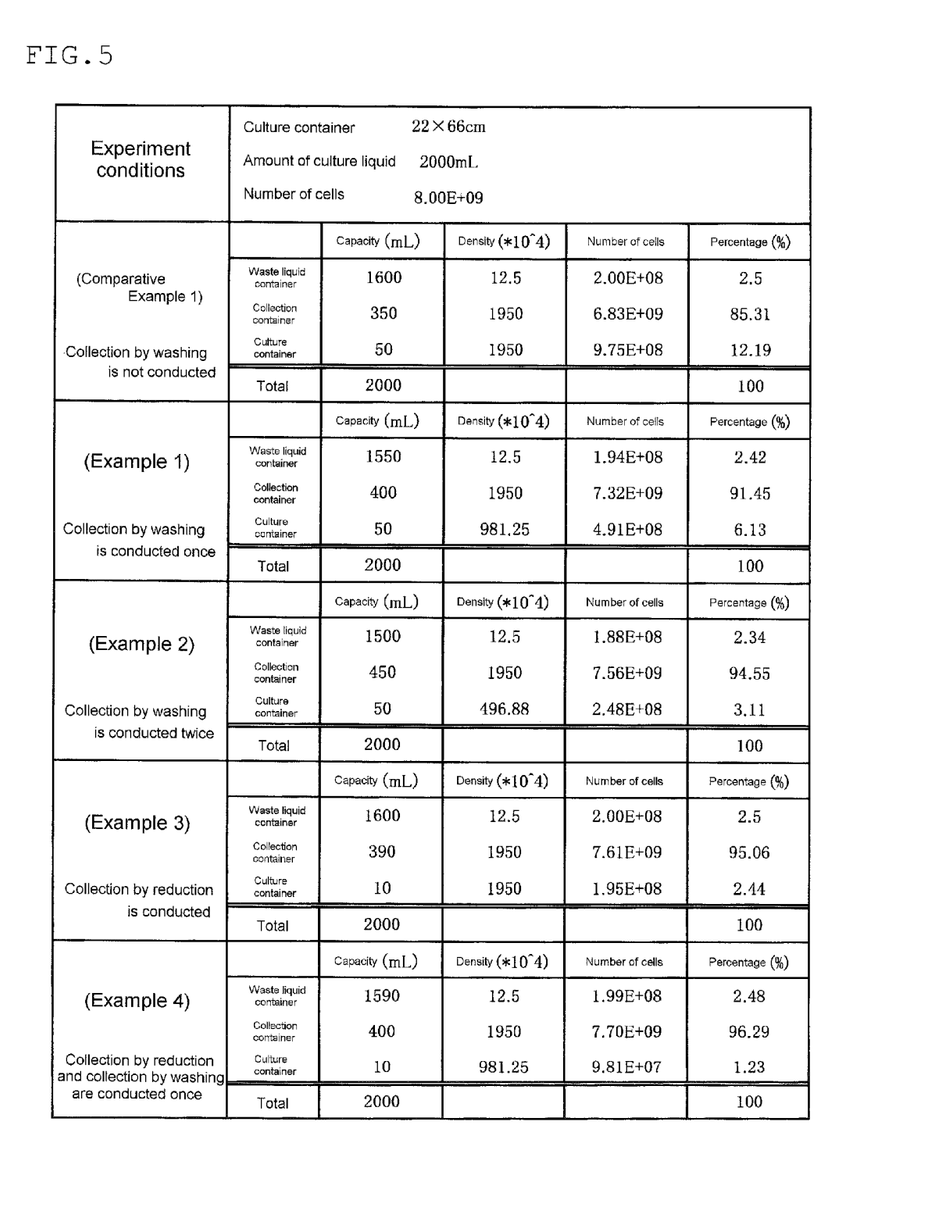
FIG. 5 is a view showing the results of an examination by the method of collecting cells of the embodiments of the present invention.

Comparison was made between a case where cells are collected from the culture container after collection by washing and/or collection by reduction in the method for collecting cells of the above-mentioned embodiment and a case where cells are collected from the culture container without conducing collection by washing and/or collection by reduction. Advantageous effects thereof were evaluated. The results are shown in FIG. 5. This experiment was conducted by using a culture container having a dimension of 22×66 cm. In this container, 2000 mL of a culture liquid and 8.00E+09 cells were sealed.

Comparative Example 1

Cells were collected from the culture container by conducting only the supernatant discharge step and the cell collection step in the method for collecting cells of the first embodiment without conducting collection by reduction and collection by washing.

It was found that the amount of the culture supernatant discharged in the waste liquid container was 1600 mL that contained 2.00E+08 cells. The percentage of these cells was 2.5%. The amount of a suspension of cells collected in the cell collection container was 350 mL that contained 6.83E+09 cells. The percentage of these cells was 85.31%. The amount of a suspension of cells remaining in the culture container was 50 mL that contained 9.75E+08 cells. The percentage of these cells was 12.19%.

Example 1

Cells were collected from the culture container by conducting each of the supernatant discharge step, the cell collection step, the supernatant returning step and the re-collection step in the method for collecting cells of the first embodiment once, whereby collection by washing was conducted once.

It was found that the amount of the culture supernatant discharged in the waste liquid container was 1550 mL that contained 1.94E+08 cells. The percentage of these cells was 2.42%. The amount of a suspension of cells collected in the cell collection container was 400 mL that contained 7.32E+09 cells. The percentage of these cells was 91.45%. The amount of a suspension of cells remaining in the culture container was 50 mL that contained 4.91E+08 cells. The percentage of these cells was 6.13%.

Example 2

Cells were collected from the culture container by conducting each of the supernatant discharge step, the cell collection step, the supernatant returning step and the re-collection step in the method for collecting cells of the first embodiment once, and by repeating the supernatant returning step and the re-collection step once, whereby collection by washing was conducted twice.

It was found that the amount of the culture supernatant discharged in the waste liquid container was 1500 mL that contained 1.88E+08 cells. The percentage of these cells was 2.34%. The amount of a suspension of cells collected in the cell collection container was 450 mL that contained 7.56E+09 cells. The percentage of these cells was 94.55%. The amount of a suspension of cells remaining in the culture container was 50 mL that contained 2.48E+08 cells. The percentage of these cells was 3.11%.

Example 3

Cells were collected from the culture container by conducting each of the supernatant discharge step, the reduction step and the collection by reduction step in the method for collecting cells of the third embodiment once, whereby collection by reduction was conducted once.

It was found that the amount of the culture supernatant discharged in the waste liquid container was 1600 mL that contained 2.00E+08 cells. The percentage of these cells was 2.5%. The amount of a suspension of cells collected in the cell collection container was 390 mL that contained 7.61E+09 cells. The percentage of these cells was 95.06%. The amount of a suspension of cells remaining in the culture container was 10 mL that contained 1.95E+08 cells. The percentage of these cells was 2.44%.

Example 4

By combining the method for collecting cells of the first embodiments and that of the third embodiment, cells were collected from the culture container by conducing each of the supernatant discharge step, the reduction step and the collection by reduction step once, and by conducting each of the supernatant returning step and the re-collection step once, whereby collection by washing is conducted once.

It was found that the amount of the culture supernatant discharged in the waste liquid container was 1590 mL that contained 1.99E+08 cells. The percentage of these cells was 2.48%. The amount of a suspension of cells collected in the cell collection container was 400 mL that contained 7.70E+09 cells. The percentage of these cells was 96.29%. The amount of a suspension of cells remaining in the culture container was 10 mL that contained 9.81E+07 cells. The percentage of these cells was 1.23%.

In Comparative Example 1, 50 ml of a suspension of cells remained in the culture container. The reason therefor is that, the culture container was blocked due to a decrease in the amount of the liquid, whereby further transfer of a suspension of cells to the cell collection container could not be conducted.

In Example 1, after a suspension of cells remained in the culture liquid in an amount of 50 ml, 50 ml of a culture supernatant was returned from the waste liquid container to the culture container, and the culture container was washed by stirring, and 50 ml of a suspension of cells was collected in the cell collection container. As a result, 50 ml of a suspension of cells remained in the culture container. In Example 2, supernatant returning and re-collection in Example 1 was further repeated once, whereby collection by washing was conducted twice.

In Example 3, by collecting a suspension of cells by reducing the bottom surface area of the culture container 10, blocking of the culture container was suppressed, whereby the amount of a suspension of cells remaining in the culture container was reduced to 10 ml.

In Example 4, after collecting a suspension of cells by reducing the bottom surface area of the culture container 10, 10 ml of a culture supernatant was returned from the waste liquid container to the culture container, and the culture container was washed by stirring, whereby 10 ml of a suspension of cells was further collected in the cell collection container. As a result, 10 ml of a suspension of cells remained in the culture container.

In Comparative Example 1, Example 1, Example 2, Example 3 and Example 4, the percentage of the number of cells collected in the cell collection container was 85.31%, 91.45%, 94.55%, 95.06% and 96.29%, respectively.

In Comparative Example 1, Example 1, Example 2, Example 3 and Example 4, the percentage of the number of cells discharged in the waste liquid container was 2.5%, 2.42%, 2.34%, 2.5% and 2.48%, respectively.

Further, in Comparative Example 1, Example 1, Example 2, Example 3 and Example 4, the percentage of the number of cells remaining in the culture container was 12.19%, 6.13%, 3.11%, 2.44% and 1.23%, respectively.

As mentioned above, cell collection efficiency of Example 1 in which collection by washing was conducted only once was increased by 6% or more as compared with that in Comparative Example 1. Cell collection efficiency of Example 2 in which collection by washing was conducted twice was increased by 9% or more as compared with Comparative Example 1.

Cell collection efficiency of Example 3 in which collection by reduction was conducted was increased nearly 10% as compared with Comparative Example 1.

Further, cell collection efficiency of Example 4 in which collection by reduction and collection by washing were conducted once was increased by nearly 11% as compared with that in Comparative Example 1.

From the results mentioned above, it can be understood that, by conducting collection by washing in the method for collecting cells of this embodiment, cell collection efficiency was increased without using a new culture medium or a washing liquid for washing purposes. By conducting collection by reduction in the method for collecting cells of this embodiment, cell collection efficiency was significantly increased. Accordingly, according to the collection by reduction in the method for collecting cells of this embodiment, blocking of the culture container can be suppressed to decrease the amount of a suspension of cells remaining in the culture container, whereby cell collection efficiency can be significantly improved.

The present invention is not restricted to the above-mentioned embodiments, and it is needless to say various modifications are possible within the scope of the present invention.

For example, in FIG. 2, the supernatant returning step was conducted by means of a roller-type stirring element. However, stirring of the culture container may be conducted by other methods such as shaking the mounting table. In addition, collection by washing may be conducted three or more times.

INDUSTRIAL APPLICABILITY

The present invention can be preferably used in the fields of biomedicines, regenerative therapy, immune therapy or the like where a large amount of cells is required to be cultivated.

The invention claimed is:

1. A method for collecting cultured cells by using a cell culture kit comprising a culture container for cultivating cells, a cell collection container for collecting cells after cultivation and a waste liquid container for collecting a culture medium after cultivation, wherein the culture container, the cell collection container, and the waste liquid container are linked to one another through a conduit, the method comprising:
   discharging a culture supernatant by transferring the culture supernatant from the culture container to the waste liquid container to obtain a concentrated suspension;
   collecting cells by transferring the concentrated suspension of the cultured cells from the culture container to the cell collection container;
   returning part of the culture supernatant that had been discharged into the waste liquid container to the culture container to allow cells remaining in the culture container to be suspended in a suspension of cells; and
   re-collecting the cells remaining in the culture container by transferring the suspension of the cells from the culture container to the cell collection container.

2. The method according to claim 1, wherein, in the returning, the cells remaining in the culture container are dispersed in the suspension of the cells while pressing a surface of the culture container until the surface of the culture container is lowered to a predetermined depth by a stirring element and moving the stirring element reciprocally in a horizontal direction on the culture container.

3. The method according to claim 2, wherein the dispersing of the cells in the returning and the transferring of the suspension in the re-collecting are conducted simultaneously.

4. The method according to claim 1, wherein the returning and the re-collecting are repeated twice or more.

5. The method according to claim 1, wherein the waste liquid container is a culture medium storage container.

6. The method according to claim 1, further comprising, prior to discharging a culture supernatant:
   reducing an inner bottom surface area of the culture container, wherein the reducing is performed by moving a partition element on the culture container while pressing the culture container by the partition element from the end portion thereof to bring an upper surface and a lower surface thereof into close contact with each other, and
   settling the cultured cells in the culture container by standing still after the reducing.

7. A method for collecting cultured cells by using a cell culture kit comprising a culture container for cultivating cells, a cell collection container for collecting cells after cultivation and a waste liquid container for collecting a culture medium after cultivation, wherein the culture container, the cell collection container, and the waste liquid container are linked to one another through a conduit, the method comprising:
   discharging a culture supernatant by transferring the culture supernatant from the culture container to the waste liquid container to obtain a concentrated suspension;
   reducing an inner bottom surface area of the culture container to gather the concentrated suspension of the cultured cells to a cell collection port side of the culture container, wherein the reducing is performed by moving a partition element on the culture container while pressing the culture container by the partition element from the outside of a cultivation space to bring an upper surface and a lower surface thereof into close contact with each other; and
   collecting the gathered suspension by transferring the concentrated suspension from the culture container to the cell collection container.

8. The method according to claim 7, wherein the gathering of the concentrated suspension of the cultured cells in the reducing and the transferring of the concentrated suspension in the collecting are conducted simultaneously.

9. The method according to claim 7, further comprising collecting cells by transferring the concentrated suspension of the cultured cells from the culture container to the cell collection container, wherein the collecting is performed after the discharging and is followed by the reducing.

10. The method according to claim 7, further comprising, after collecting the gathered suspension:
- returning part of the culture supernatant that had been discharged into the waste liquid container to the culture container to allow cells remaining in the culture container to be suspended in a suspension of cells; and
- re-collecting the cells remaining in the culture container by transferring the suspension of the cells from the culture container to the cell collection container.

11. The method according to claim 7, wherein the partition element is a roller.

* * * * *